United States Patent [19]

Boon

[11] Patent Number: 4,802,850
[45] Date of Patent: Feb. 7, 1989

[54] DENTAL-PORCELAIN COLOR MATCHING SYSTEM

[76] Inventor: David G. Boon, Pinhays, Herring Road, South Pool, Kingsbridge, S. Devon, United Kingdom

[21] Appl. No.: 41,834

[22] Filed: Apr. 21, 1987

[30] Foreign Application Priority Data

Apr. 22, 1986 [GB] United Kingdom ............... 8609778

[51] Int. Cl.⁴ .................................................... A61C 19/10
[52] U.S. Cl. ........................................................ 433/26
[58] Field of Search ................................... 433/25, 26

[56] References Cited

U.S. PATENT DOCUMENTS

| | | | |
|---|---|---|---|
| 785,992 | 3/1905 | Whiteley | 433/26 |
| 1,565,244 | 12/1925 | Angell | 433/26 |
| 1,709,066 | 4/1929 | Field | 433/26 |
| 2,805,475 | 9/1957 | Adams | 433/26 |
| 4,115,922 | 9/1978 | Alderman | 433/26 |

FOREIGN PATENT DOCUMENTS 0169093 10/1951 Fed. Rep. of Germany ........ 433/26

OTHER PUBLICATIONS

"The Key to New Trubyte Shades", Nov. 30, 1936.

*Primary Examiner*—John J. Wilson
*Assistant Examiner*—Adriene J. Lepiane
*Attorney, Agent, or Firm*—Thomas J. Greer, Jr.

[57] ABSTRACT

A dental-porcelain color matching system comprises a plurality of dental-porcelain beads arranged in a closely spaced manner on a common support so that their colors vary in an ordered manner. The beads are carried at the ends of arms which are either flexible or pivotable on a main trunk of the support so that a bead to be located against a patent's natural tooth for color comparison therewith can be moved away from other beads on the support to avoid color interference therefrom. Additional beads provided have varying translucent enamels on opaque porcelain bases to allow the color, translucency and depth of enamel of a patient's teeth to be gauged. The beads also vary in shape from that of an unworn natural incisor tooth with a ridged cutting edge to that of a worn incisor tooth with a smooth cutting edge.

3 Claims, 4 Drawing Sheets

DENTAL-PORCELAIN COLOR MATCHING SYSTEM

BACKGROUND OF THE INVENTION

The present invention relates to a colour-matching system particularly for use in matching the colour of a dental prosthesis to that of an adjacent tooth.

In this specification the term colour will be used to include the different hues, such as red, yellow, green and orange, and also different tints or shades of the various hues in which the pure hue is modified by the admixture of white and/or black pigment in varying degrees.

Although the predominant hue of natural teeth is yellow, the variations between a very pale cream and greyish brown are infinite and dental porcelains are now available in a wide variety of different colours in order to allow dental prostheses to be matched closely to the colour of adjacent teeth in a patient's mouth. This colour matching is generally effected with the aid of samples of the different coloured porcelains, each provided in the form of a tiny bead, or button, on a respective spatula-like carrier. These are placed successively in a patient's mouth, close to a tooth which will be adjacent the prosthesis when fitted, until a good colour match is found.

A problem with this known system is that the multitude of spatulas needed occupies considerable bulk and is not easy to store in a simple system which allows them to be replaced in order quickly after use. Indeed, the normal practice is for a dental surgeon to remove several spatulas from the system at a time and to put them down temporarily on any convenient surface; the spatulas inevitably get muddled and considerable time is wasted in sorting and replacement in the system after use.

A further difficulty with the use of spatulas is that they are normally stiff and opaque so that it is not easy to locate them in the patient's mouth, close enough to a tooth for colour matching, without also obstructing the light to the tooth. In this respect, the problems of lighting a patient's mouth and the effects on colour perception of even slight shadows are well known.

SUMMARY OF THE INVENTION

The object of the present invention is to provide a range of dental porcelain samples for colour matching in a form which is more convenient to use than current systems.

Accordingly, the present invention provides a dental-porcelain colour-matching system comprising a plurality of dental porcelain beads of different colours carried on a support adapted to allow beads to be moved apart so that each bead can be placed individually against a patient's natural tooth without colour interference from any other bead on the support.

In order for the beads to be movable relative to each other they may be mounted on a flexible and/or resilient support, preferably of plastics material, or the support may be formed in several interengaged parts which are movable relative to each other. They may, for example, be mutually telescopic or pivotable. Whatever form of movement is allowed, the beads may be located very close together (of the order of a few mm or even touching in some embodiments) in the rest or stored condition of the system so that the overall bulk of the stored system may be less than that of a spatula system having the same number of beads.

The beads may be releasable from the support, or individual beads or groups of beads may be carried on support parts releasably engageable with the main body of the support, so that beads may be interchangeable to vary the colour range provided in a system but, during use by the dental surgeon, the beads are preferably retained on the common support so that they cannot get mixed up; this relieves the surgeon or his technician of the time-wasting task of sorting after use.

The beads themselves may be of the usual button shape, about 3 mm to 8 mm in diameter, or of other convenient shape such as pear or tooth shape. From about 8 to 60 beads may conveniently be provided on any one support, additional supports being provided for further beads, if required.

The beads are preferably arranged in an ordered manner in terms of gradation of colour, the arrangement depending on the shape of the support; three-dimensional arrangements are certainly possible although essentially two-dimensional arrays, which enable all the beads to be seen to facilitate selection by the dental surgeon, are preferred. In the case of flexible supports without interengageable parts, two-dimensional arrangements are particularly convenient since the support may then be made simply and cheaply in sheet form, preferably from sterilizable, washable plastics material. In such cases the support is preferably branched, beads being carried on the branches which may be moved apart to facilitate the location of individual beads against a tooth in use.

Beads may also be located on the trunk, or spine, of the support or on fingers projecting into apertures or spaces on or adjacent the spine and flexible out of the plane of the spine to allow colour comparison of respective beads with a tooth.

In alternative embodiments in which the support has interengaged parts which are movable relative to each other, the support may also have a spine and arms extending therefrom to support beads at their free ends. In a preferred embodiment, each arm is pivotable relative to the spine from a stored position in which it lies alongside the spine and adjacent other arms to a position of use in which it projects from the spine and its button is sufficiently spaced from other buttons for comprison with a tooth. Each arm may be pivotable individually or combined in a group with other arms pivotable as a group.

In embodiments with interengaged parts, these may be made from the same or different materials. A spine part may, for example, be of metal, preferably stainless steel or brass, or of plastics material (thermosetting or thermoplastics) and is preferably sufficiently thick to be fairly rigid. The arms, on the other hand, are preferably of plastics material, and may be rigid or flexible or possibly of graduated thickness such that the end attached to the spine is relatively rigid while the free end carrying the bead is fairly flexible.

The support, or central part of the support, of the present invention may be opaque but at least the parts carrying the beads are preferably transparent or translucent to minimize the obstruction of light to a patient's mouth, in use. A translucent material is preferred since this may be white, or an extremely pale colour, to provide a convenient background which facilitates the colour matching of a bead with a tooth. Each bead on a support is preferably identified by a reference which may be printed on, glued to or otherwise provided on or adjacent the respective bead on the front or reverse side of the support.

The beads may be attached to the support in any convenient manner; for example they may be snap-engageable with the support, glued to the support or embedded in it during manufacture of the support.

If a crowned tooth having a metal core is to be made, the porcelain beads are preferably metal-backed to facilitate and improve the colour matching achievable. The backing may comprise a thin foil or a metal plate, stud or rivet by which the bead can be attached to the support. The bead is preferably glued to the metal.

The beads themselves may also comprise several porcelain layers of different colours since both teeth and modern dental prostheses include several layers. In particular, the system of the invention may further include a set of beads comprising different thicknesses of substantially colourless, transparent or translucent ceramic, simulating dental enamel, over an opaque base to facilitate the matching of the enamel thickness in a dental prothesis with that of the patient's teeth. In this case, the beads are preferably generally tooth shaped and the transparent layers may be formed to simulate different stages in the wear of natural teeth.

A further set of beads may also be provided, each bead comprising an opaque dental-porcelain base with a coating of translucent enamel, the enamel coating of the beads varying in translucency and/or colour so that the beads may be compared with a natural tooth to obtain an estimate of the translucency and/or colour of the tooth enamel for the making of a dental prosthesis.

Sets of dental-porcelain beads displaying different enamel layers as indicated above, are not themselves known and can be incorporated in any dental-porcelain colour-matching system.

BRIEF DESCRIPTION OF THE DRAWINGS

Several embodiments of the invention will now be more particularly described, by way of example, with reference to the accompanying drawings, in which.

DETAILED DESCRIPTION OF THE INVENTION

Figure 1:
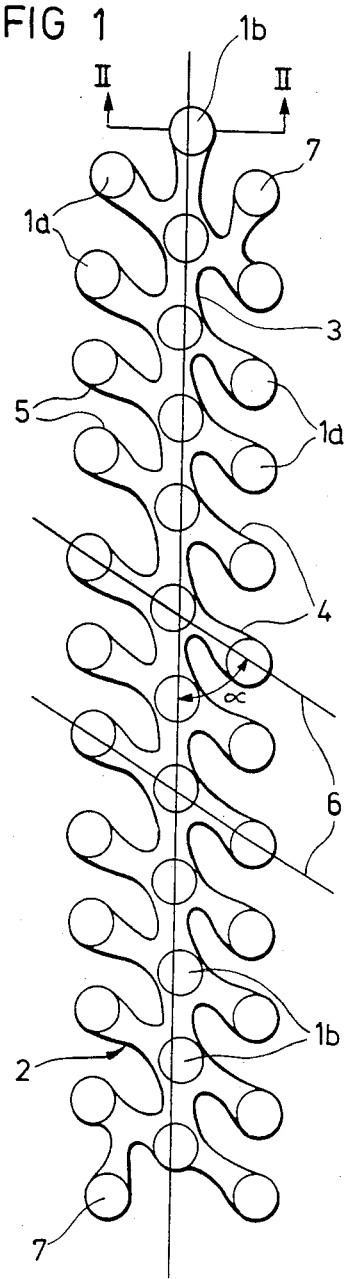
FIG. 1 is a top plan view of a dental-porcelain colour matching system according to a first embodiment of the invention.

With reference to FIG. 1 of the drawings, a dental-porcelain colour-matching system is shown comprising a plurality of button-shaped porcelain beads 1 of different colours carried on one surface, which will be termed the upper surface, of a generally-flat, translucent, white, plastics support 2 having a uniform thickness of 2–3 mm. The beads are generally designated as 1 and are either beads 1a of the free arms 4 and 5, or beads 16 centrally located. In practice several such "systems" would be provided to display the entire range of dental porcelain colours available.

The support 2 is moulded from resiliently-flexible silicone rubber or polyurethane and comprises a central spine 3 with arms 4 and 5 projecting from respective opposite sides thereof. The arms 4 and 5 are substantially equispaced along the spine 3 and are inclined in opposite directions to its longitudinal axis, each arm 4 lying substantially on a respective common axis 6 with one of the arms 5. The angle between the axes 6 and the axis of the spine 3 is conveniently about 60°.

Each arm 4, 5 carries a porcelain bead 1a at its free end and further porcelain beads 1b are spaced apart along the spine 3 substantially at the junction of a pair of arms 4, 5 lying on a common axis 6 with the spine 3. The length of the arms 4, 5 is such that the spacing between each bead 1a and the adjacent bead 1b on the spine and the spacing of adjacent beads 1b on the spine itself is substantially the same: the beads 1 are circular, with a diameter of about 8 mm and the distance between the centres of adjacent beads 1 is about 17 mm.

In this embodiment there are twelve central beads 1b and eleven on each of the arms 4 and 5 giving a total of 34 beads. In order to provide a convenient total of 36 beads 1, two additional arms 7, are provided, one at each end of the spine 3, the arms 7 projecting from the end arm 4 at one end and from the end arm 5 at the other. This gives the system a convenient total length of about 190 mm, but clearly any number of beads 1 may be provided in such a system on an appropriate length of the support 2.

Figure 4:
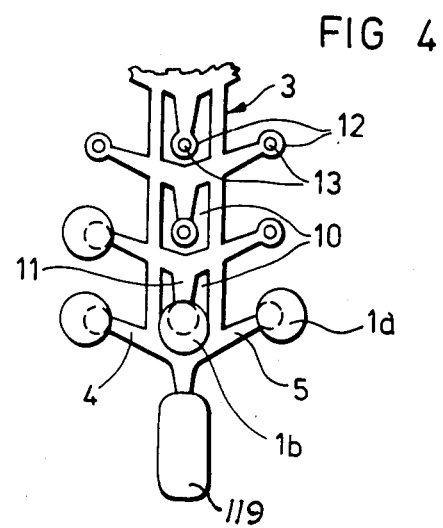
FIG. 4 is a top plan view of part of a third embodiment of a dental-porcelain colour-matching system of the invention.

It will be seen from FIG. 4 of the drawings that the cross-section of the support 2 widens upwardly: this is to facilitate removal of the support from the mould during manufacture. The support is also formed with rounded corners where the arms 4 and 5 join the spine 3 both to facilitate moulding and, with the slight narrowing of the spine and arm parts not directly carrying the beads, to facilitate flexing of the support in its own plane, without tearing, in use.

The beads 1 are attached to the support 2 during moulding, the beads simply being placed in their correct positions on the upper surface of the support before curing of the support. The beads could, alternatively, be glued or otherwise attached to the finished support.

As the beads 1 are located on the support 2, they are arranged in an ordered manner in terms of colour. For example, the beads 1 may all be of substantially the same hue, or of closely related hues; beads of more different hues may be provided on additional supports. On each individual support the beads will vary in shade or tint, from lighter to darker, in a regular manner.

In particular, in each group of three beads 1 aligned on a common axis 6, the central bead 1b may be intermediate in shade between the shades of the outer beads 1a. The colours of the beads 1 are identified by respective reference numbers 8 moulded in the undersurface of the support 2.

In use of the system described above, a dental surgeon may hold the support 2 to place each porcelain bead 1 in turn against a patient's tooth the colour of which is to be matched in the making of a dental prosthesis. The flexibility of the support allows outer beads 1a on the arms 4 and 5 to be kept out of the way while central beads 1b are located against the tooth, bearing in mind the graduated arrangement of the colours, however, it may not be necessary to test the central bead colours and, indeed, these central beads, with the intermediate shades, may be omitted altogether from the system.

It should be noted that the translucent support 2 does not obstruct light entering the mouth substantially and its whiteness allows slight differences in colour between a porcelain bead and a tooth being matched to be perceived. The support may, however, have a slight blue or pink tinge since such a background colour, provided it is not too strong, would enhance the perception of yellow and facilitate the comparison of closely matched grey-yellow shades.

It will be appreciated that the system is washable and can be sterilized.

Figure 3:
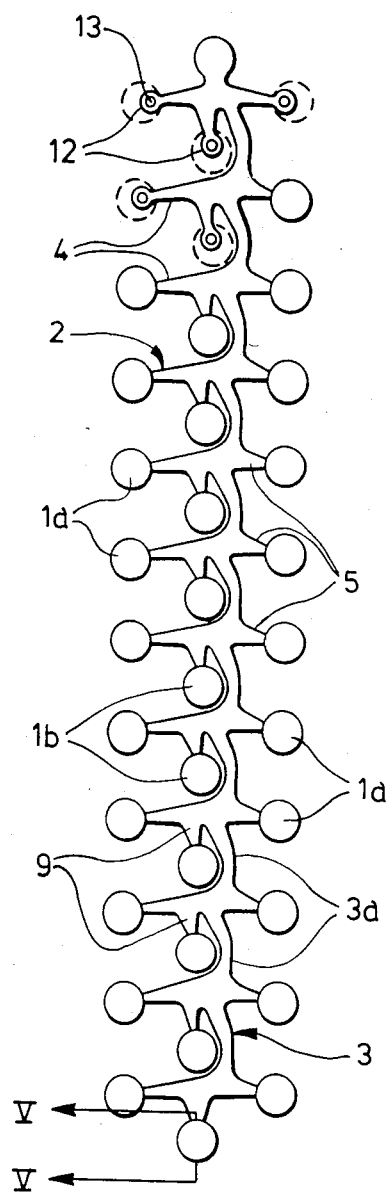
FIG. 3 is a top plan view of a second embodiment of a dental-porcelain colour matching system of the invention with some of the porcelain beads removed.

With reference now to FIGS. 3 and 4 of the drawings, two alternative dental-porcelain colour matching systems are shown with similar features to those of the embodiment of FIG. 1 indicated by the same reference numerals. These embodiments differ from that of FIG. 1 in the shape of the support 2 and in the mode of attachment of the porcelain beads 1 to the support 2.

In the embodiment of FIG. 3, it will be seen that the central beads 1b are each carried on a finger 9 branching from a respective arm 4 of the support 2, the arms 4 being longer than the arms 5. The fingers 9 all lie on the same side of the support spine 3 and project in the same direction from the arms 4, substantially parallel to the longitudinal axis of the support 1. Portions 3a of the spine 3 between adjacent arms 4 are curved to accommodate the fingers 9.

In the embodiment of FIG. 4, the central spine 3 is broadened compared with that of FIG. 1 and formed with apertures 10, the central beads 1b being carried on fingers 11 which project into the apertures 10, parallel to the longitudinal axis of the support 2. The arms 4 and 5 are also arranged in pairs projecting with mirror symmetry one on either side of the spine 3.

Figure 2:
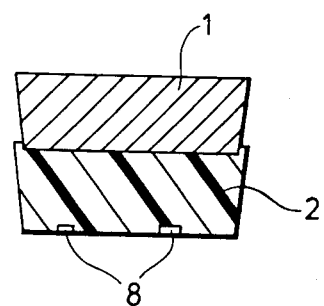
FIG. 2 is a cross-sectional view, on an enlarged scale, taken on line II—II of FIG. 1.

In use of the embodiments of FIGS. 3 and 4, the central beads 1b can be located more easily and conveniently against a tooth to be matched than in the case of the first embodiment of FIGS. 1 and 2.

The beads 1 of embodiments similar to those of FIGS. 3 and 4 could be attached to the support 2 in a similar manner to that shown in FIG. 2 but FIGS. 3 to 6 show alternative methods of attachment. For this purpose, the support arms 4 and 5 and fingers 9 taper towards their ends then widen into generally-circular pads 12 with circular apertures 13 extending from the top to bottom surfaces.

Figure 5:
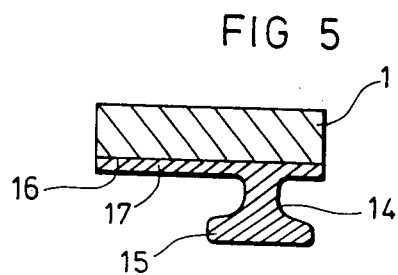
FIGS. 5 and 6 are enlarged sectional views of respective alternative porcelain beads for use in the systems of FIGS. 3 and 4, taken on a line corresponding to line V—V FIG. 3.

Each bead 1 may be formed with a stem 14 projecting from its under surface and widening into a head 15, like a press- or collar stud. The support 2 is sufficiently resilient and deformable to allow the head 15, which has a slightly larger diameter than the apertures 13, to be forced through such an aperture 13 and then relaxes slightly to grip the stem 14 and retain the bead 1 on the support 2. The entire bead 1 may be made from dental ceramics or alternatively, as shown in FIG. 5, the bead 1 may have a flat back surface 16 and the stem 14 and the head 15 may be made from metal with a plate 17 which is glued to the back surface 16 of the bead 1, preferably with an epoxy resin.

Figure 6:
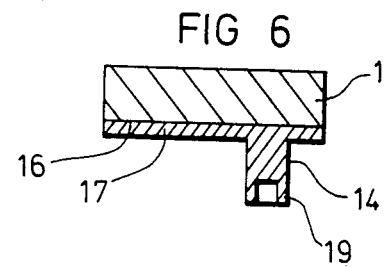

In the alternative shown in FIG. 6, the bead 1 is glued to a metal plate 17 which carries a stem 14 with an axial collar 19 which can be upset once the stem 14 has been passed through an aperture 13 to rivet the bead 1 to the support 2.

In the embodiments of FIGS. 3-6, the beads 1 are provided with attachment stems 14 which are offset from their centres, for convenience, although in alternative embodiments the stems 14 could be placed centrally.

In the embodiment of FIG. 4, one end of the support 2 has a label 119 attached to it in a similar manner to the beads 1 for information regarding the beads 1 on that support 2.

Figure 7:
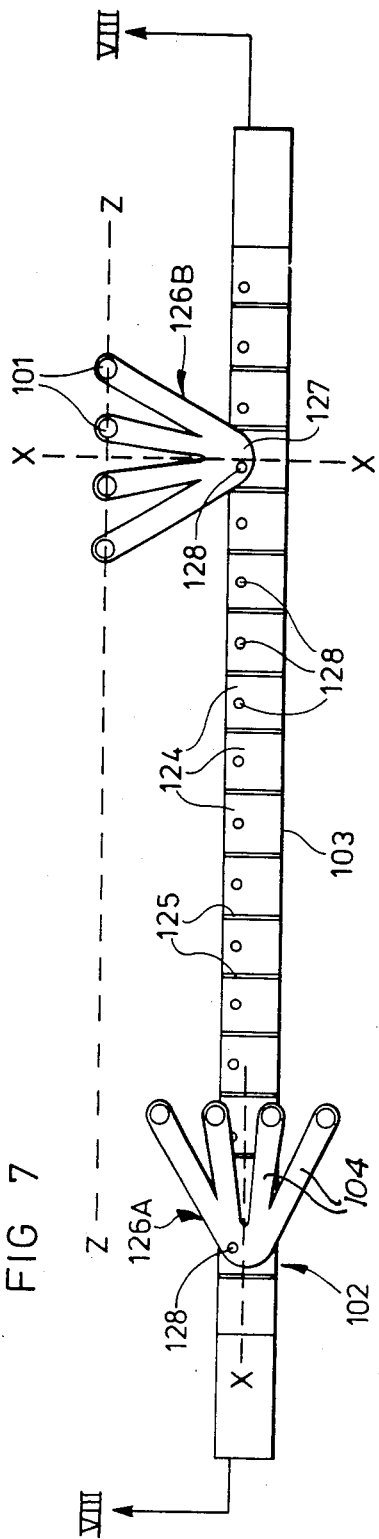
FIG. 7 is a top plan view of part of a dental colour-matching system according to a fourth embodiment of the invention.
Figure 8:
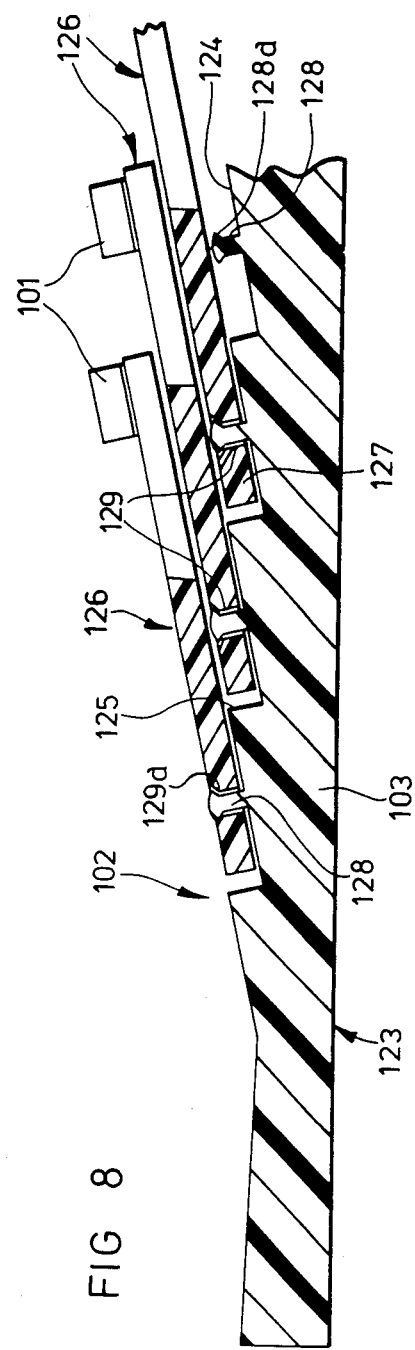
FIG. 8 is a longitudinal-sectional view of part of the system of FIG. 7 on an enlarged scale, taken on the line VIII—VIII of FIG. 7.

With reference to FIGS. 7 and 8 of the drawings, a further embodiment of the invention is shown in which features similar to those of FIGS. 1 and 2 are indicated by the same reference numberal increased by 100.

In FIGS. 7 and 8, a dental porcelain colour-matching system is shown which includes a support generally indicated 102 carrying a plurality of porcelain beads 101. The support 102 is formed in several interengaged parts, the main part comprising an elongate spine 103 having a flat, elongate, rectangular lower surface 123 and a stepped upper surface defining approximately square, parallel bearing surfaces 124 inclined at a small angle of about 5° to the lower surface 123. The bearing surfaces 124 are approximately 9 mm square and are interconnected by risers 125, approximately 1 mm deep.

The subsidiary parts of the support 102 comprise a plurality of generally flat, straight, support arms, each indicated 104, arranged in identical groups of four, each generally indicated 126. The four support arms 104 in each group 126 lie in a common plane and are joined at a common end 127 from which they extend fanwise, two on each side of a line of mirror symmetry indicated X—X, each arm 104 carrying a dental porcelain bead 101 at its free end. Each bead 101 may be attached to its support arm 104 by any of the methods described above with reference to FIGS. 2 to 6, but the use of a metal backing plate and central rivet (rather than the offset rivet of FIG. 6) is preferred.

Each group 126 is pivotally attached to the spine 103 at the common end 127 for pivotal movement in its own plane, each on a respective bearing surface, or step, 124 on the spine 103. Normally there would be as many groups 126 in the system as steps 124, but only a few groups are shown in the drawings.

The pivotal attachment of each arm group 126 to a respective step 124 is achieved by means of a pin 128 projecting from the step 124, perpendicular to its surface, and engaged in a through hole 129 in the end 177. The pin 128 has a slightly enlarged head 128a and the hole 129 has a widened end seat 129a such that the head 128a is snap engageable through the hole 129 in the seat 129a to retain the group 126 on the spine 103. Each group 126 may alternatively carry a pivot pin which is engageable in an aperture in a respective step 124 or may be pivoted on the step in any other convenient manner, such as by a rivet, and may be permanently captive on the spine 103 or readily releasable therefrom.

As is best seen in FIG. 7, the pins 128 do not lie along the longitudinal axis of the spine 103 but are offset to one side of it, all the pins 128 lying on a single straight line. Similarly, each pivot hole 128 is offset to one side of the axis X—X of its arm group 126; each end 127 is also rounded. This configuration allows each arm group 126 to be pivoted on its step 124 from a stored position, in which its axis X—X is substantially aligned with the longitudinal axis of the spine 103 (as shown by the arm group, indicated 126A, in the left-hand side of FIG. 7) to a position of use, in which its axis X—X is substantially at right angles to the axis of the spine 103 (as shown by the arm group, indicated 126B, in the right-hand side of in FIG. 7).

As is seen in FIG. 8, when the arm groups 126 are in their stored positions, they overlap each other and lie on the spine 103 in a very compact configuration. In their positions of use, however, as shown by the group 126B in FIG. 7, the free ends of their arms 104 are remote from the spine 103 and from the stored groups 126; the arms 104 are of such a length, the two outer arms of the fan being longer than the inner ones, that the beads 101 on any one arm group 126 lie on a straight line, indicated by the broken line Z—Z in FIG. 7, which does not intersect the arms 104 of the stored groups 126. In this position of use, the dental porcelain beads 101 can be placed against a tooth, the colour of which is to be matched, without colour interference from any of the other beads 101 on the support 102.

In the embodiment of FIGS. 7 and 8, the spine 103 is substantially rigid and may be made from metal or plastics material, preferably NYLON ( Registered Trade Mark). The arms 104 are preferably of pale-coloured, translucent plastics material for reasons explained earlier in this specification. In the embodiment shown, the arms 104 are generally rigid and cannot be flexed in their own plane, but have sufficient flexibility to be flexed out of this plane to facilitate individual location against a tooth.

In FIGS. 7 and 8, a spine 103 is shown with twenty-one steps 124 which can accommodate the same number of groups 126, giving a total of eighty-four buttons. These can conveniently be divided into three groups of twenty-eight buttons displaying different dental-porclain colours, as indicated in FIG. 9.

Figure 9:
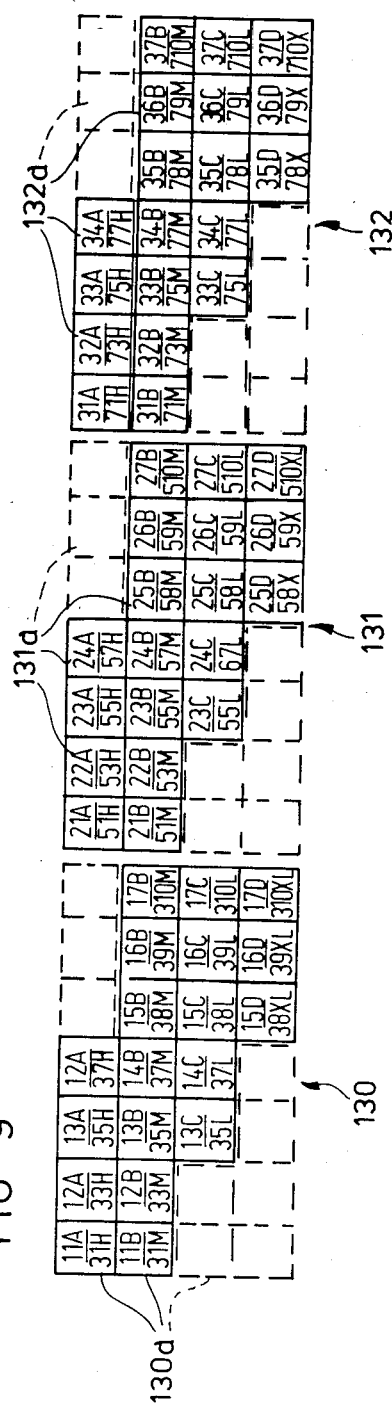
FIG. 9 is a chart showing a range of dental porcelain colours which may be displayed with the system of FIGS. 7 and 8.

With reference to FIG. 9, a dental porcelain colour chart is shown which is divided into three main areas 130, 131 and 132, each subdivided into four lines of seven subareas, several of the latter denoted by the numerals 130a, 131a and 132a. The areas 130, 131, 132 display colours with a predominantly red, yellow or blue hue respectively, the subareas within each main area displaying variations in the respective colour arranged in an ordered manner. In the chart shown, the hue increases in strength from left to right and in its degree of greyness (i.e. quantity of black pigment added) varies from top to bottom.

The chart of FIG. 9, with eighty-four different colours, was worked out to cover practically the entire range of colours found in natural teeth but it was subsequently found that certain colours, at the extremes of the three colour groups 130, 131, 132, were sufficiently rare to be omitted from the system. These extreme colours are shown in broken outline in FIG. 9 and, when omitted, reduce the number of subareas to the more manageable number of sixty. These remaining subareas, shown in full outline, are each given an identification index, 11A/31H . . . 37D/710X, corresponding to a respective dental porcelain colour.

It will be appreciated that, if only sixty colours are to be displayed by the buttons 101 in the system of FIGS. 7 and 8, not all the support arms 104 will be used. In order to keep these colours in the ordered arrangement shown in the chart of FIG. 9, it is preferred to provide groups 126 with only two or three arms 104, as appropriate, rather than to provide a smaller number of the groups 126, each with four arms 104. These groups 126, with two or three arms 104, may be preformed as such but, to simplify manufacture, identical groups of four arms are preferably formed and the unwanted arms are then cut away.

It should be noted that, with the system of FIGS. 7 and 8, although the arm groups 126 overlap each other in their stored position, so that the stored system is very compact, all the buttons 102 are in fact visible so that a dental surgeon can easily select buttons for matching with a patient's tooth, in use.

Figure 10:
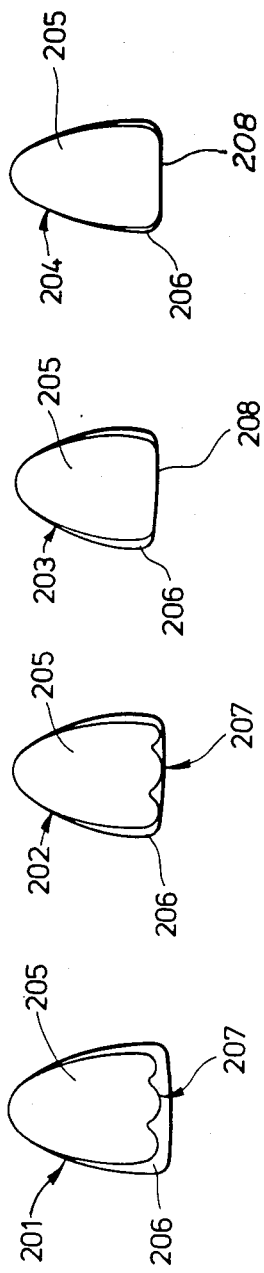
FIG. 10 is a top plan view of additional porcelain beads which may be incorporated in the systems of FIGS. 1 to 8.

With reference now to FIG. 10 of the drawings, this shows additional porcelain beads 201, 202, 203 and 204 which can be incorporated in any dental porcelain colour matching system for estimation of the enamel-dentine ratio of natural teeth. The beads 201–204 are generally tooth-shaped and are formed from an opaque dental porcelain base 205 with a covering of translucent enamel 206 to simulate the underlying dentine layer and overlying enamel layer respectively of natural teeth.

In the bead 201, the opaque base 205 has the shape of a young, unworn incisor tooth, with a ridged cutting edge 207 and a thick covering of enamel 206, whereas in the bead 204, the porcelain base 205 has the smooth cutting edge 208 of a very worn tooth and the enamel 206 forms only a thin layer on the upper and lower surfaces and side edges. The beads 202 and 203 represent stages in tooth wear intermediate those of the beads 201 and 204, the bead 202 having a slightly ridged cutting edge 207 with enamel 206 just filling the gaps between the ridges, and the bead 203 having a smooth cutting edge 208 but a thicker coating of enamel than the bead 204. Beads simulating further intermediate degrees of wear may be added to the beads 201–104.

It will be appreciated that the beads of FIG. 10 may be incorporated in any dental-porcelain colour matching system, such as those described above, either on the same support as coloured beads in the system, or on a separate support, and may be used to assist a dental surgeon to estimate the enamel-dentine ratio of a patient's natural teeth so that this can be simulated in a dental prosthesis.

The similitude of a prosthesis to natural teeth may be even further enhanced by the careful selection of the colour and degree of translucency of the enamel layer. This selection may be facilitated by the incorporation of further beads in a system of the invention to display different types of enamel. For example, four beads similar to the beads 201 may be used, but with enamels varying from very translucent to nearly opaque. A further four beads, like the beads 201, may display different coloured enamels: white; white-blue; blue; and blue-grey.

What is claimed is:

1. A set of dental porcelain beads for incorporation in a dental-porcelain color matching system, each said bead comprising an opaque dental-porcelain base in the shape of an incisor tooth with a coating of translucent enamel, at least some of said bases having the shape of the dentine layer of an unworn natural incisor tooth with a ridged cutting edge, at least some of said bases having the shape of the dentine layer of a worn incisor tooth with a smooth cutting edge, and at least some of said bases having the shape of the dentine layer in one of the successive stages between that of an unworn natural incisor tooth and a worn incisor tooth, and said enamel coatings varying in thickness so as substantially to simulate the enamel layer of the corresponding natural tooth.

2. A dental-porcelain color matching system comprising a plurality of dental-porcelain beads of different colors carried on a support adapted to allow at least some of said beads to be moved apart so that each said bead can be placed individually against a patient's natural tooth for color comparison with that tooth without color interference from any other bead on said support, wherein said support comprises an elongate body part with a stepped surface and a plurality of respective pivot points, the arms projecting from a respective said pivot point in a common plane and each arm carrying a said bead at its free end, wherein each said group is pivotally attached at its pivot point to a respective step of said stepped surface such that said groups lie in planes parallel to said steps and overlap each other in a stored condition of the system so that the beads are closely spaced but all are visible, and wherein each group is pivotable in its plane into a position for said color comparison.

3. A dental-porcelain color matching system comprising a plurality of dental-porcelain beads of different colors carried on support adapted to allow at least some of said beads to be moved apart so that each said bead can be placed individually against a patient's natural tooth for color comparison with that tooth without color interference from any other bead on said support, wherein said support is made from a material selected from flexible and flexibly-resilient materials to allow beads which are closely spaced in a relaxed condition of the support to be moved apart for said color comparison.

* * * * *